(12) United States Patent
Tsuda et al.

(10) Patent No.: US 10,175,289 B2
(45) Date of Patent: Jan. 8, 2019

(54) WATER-TREE RESISTANCE EVALUATION METHOD, INSULATION DESIGN METHOD, AND ROTARY ELECTRIC MACHINE

(71) Applicant: TOSHIBA MITSUBISHI-ELECTRIC INDUSTRIAL SYSTEMS CORPORATION, Chuo-ku (JP)

(72) Inventors: Toshihiro Tsuda, Tokyo (JP); Tetsuo Yoshimitsu, Tokyo (JP); Yuichi Tsuboi, Tokyo (JP); Yoshihiro Ishikawa, Tokyo (JP); Teruo Kanekawa, Tokyo (JP)

(73) Assignee: TOSHIBA MITSUBISHI-ELECTRIC INDUSTRIAL SYSTEMS CORPORATION, Chuo-ku (JP)

( * ) Notice: Subject to any disclaimer, the term of this patent is extended or adjusted under 35 U.S.C. 154(b) by 263 days.

(21) Appl. No.: 15/022,328

(22) PCT Filed: Sep. 20, 2013

(86) PCT No.: PCT/JP2013/005587
§ 371 (c)(1),
(2) Date: Mar. 16, 2016

(87) PCT Pub. No.: WO2015/040656
PCT Pub. Date: Mar. 26, 2015

(65) Prior Publication Data
US 2016/0223605 A1 Aug. 4, 2016

(51) Int. Cl.
*G01R 31/12* (2006.01)
*H02K 3/44* (2006.01)
(Continued)

(52) U.S. Cl.
CPC ......... *G01R 31/1272* (2013.01); *G01N 17/00* (2013.01); *G01R 31/003* (2013.01);
(Continued)

(58) Field of Classification Search
None
See application file for complete search history.

(56) References Cited

U.S. PATENT DOCUMENTS 4,212,756 A 7/1980 Ashcraft et al.
4,305,849 A 12/1981 Kawasaki et al.
(Continued)

FOREIGN PATENT DOCUMENTS

CN 101713725 A 5/2010
JP 9-251003 A 9/1997
(Continued)

OTHER PUBLICATIONS

International Search Report dated Nov. 5, 2013 in PCT/JP2013/005587 filed on Sep. 20, 2013.
(Continued)

*Primary Examiner* — Jermele M Hollington
(74) *Attorney, Agent, or Firm* — Oblon, McClelland, Maier & Neustadt, L.L.P.

(57) ABSTRACT

A water-tree resistance evaluation material including: a material selection selecting a candidate insulation material; a test carrying out a water tree test on a test piece having electrode holes formed on a first surface; and a candidate insulation material evaluation evaluating characteristics of the candidate insulation material, including progress and speed of a water tree. The test includes: a system and condition setting for setting a test system; a voltage application for grounding a ground-side electrode that is immersed in the ground-side aqueous solution, while applying an AC voltage to an application-side electrode that is immersed in the application-side aqueous solution; a measurement step; and a period determination for determining whether a test period has exceeded a predetermined period.

5 Claims, 8 Drawing Sheets

(51) Int. Cl.
*G01N 17/00* (2006.01)
*G01R 31/00* (2006.01)
*G01R 31/34* (2006.01)

(52) U.S. Cl.
CPC .......... *G01R 31/1227* (2013.01); *H02K 3/44* (2013.01); *G01R 31/34* (2013.01)

(56) References Cited

U.S. PATENT DOCUMENTS

| | | | |
|---|---|---|---|
| 10,041,990 B2 * | 8/2018 | Nakaji | ................... G01N 17/00 |
| 2014/0062525 A1 * | 3/2014 | Obata | ................ G01R 31/1272 |
| | | | 324/765.01 |
| 2017/0336466 A1 * | 11/2017 | Nakaji | ................... G01N 17/00 |

FOREIGN PATENT DOCUMENTS

| | | |
|---|---|---|
| JP | 10-321056 A | 12/1998 |
| JP | 11-172057 A | 6/1999 |
| JP | 2001-349924 A | 12/2001 |
| JP | 2010-151576 A | 7/2010 |
| JP | 2012-103158 A | 5/2012 |

OTHER PUBLICATIONS

Extended European Search Report dated Mar. 29, 2017 in Patent Application No. 13893965.7.

* cited by examiner

US 10,175,289 B2

WATER-TREE RESISTANCE EVALUATION METHOD, INSULATION DESIGN METHOD, AND ROTARY ELECTRIC MACHINE

TECHNICAL FIELD

The present invention relates to a water-tree resistance evaluation method for insulation material that is used for an insulating portion of a rotary electric machine, an insulation design method, and a rotary electric machine that uses these methods.

BACKGROUND ART

Among cables that can be used in water, conductor or copper wire of some cables is covered with an insulation portion that is made of polymer material and the like. As the polymer material, for example, thermosetting resin, such as cross-linked polyethylene which will be referred to as XLPE, is used in many cases.

The insulating cables that are laid in water include those used to propagate inverter voltage (AC voltage) and the like. Such an insulating cable could suffer water trees emerging in its insulating portion, such as XLPE, after several years of its use with AC voltage, including inverter surges. The water trees is a kind of an insulation deterioration phenomenon that occurs in the insulating material of the insulating portion, which is triggered by an electric field being applied to the insulating portion in the case that water coexist for a long time.

The water-tree phenomenon finally induces the breakdown of insulation. As the water-tree diagnosis technology, an insulation diagnosis system or the like is known (Refer to Patent Document 1): The insulation diagnosis system carries out an insulation diagnosis for lightning arresters and power cables during power systems are shut down.

In order to select the material for the insulating portion of the insulating cable laid in water or to design the structure thereof, it is necessary to understand various things in advance, including how water tree could occur. Accordingly, it is necessary to carry out a test in which water trees are generated, or reproduced, on a trial basis.

In order to generate water tree, a water electrode method or the like is used. According to the water electrode method, electrode holes are formed in an XLPE plate, which is a test piece. The test piece is then immersed in liquid, and a relatively high electric field is generated near each electrode hole. As a result, water trees are reproduced near each electrode hole of the XLPE.

Usually, in order to form each electrode hole, a mold member which has protruding portions is pushed into the XLPE plate. The electrode holes thus formed could vary each other in shape in many cases. Factors behind the shape variation need to be eliminated before water trees that have been generated around each electrode hole are evaluated. In this manner, the shape variation makes the evaluation of water trees complex.

Pushing the protruding portions into the plate causes damage to the molecular structure of the XLPE at around each electrode hole. As a result, the molecular structure of the XLPE around each electrode hole is different from the molecular structure of other parts of the XLPE. Therefore, it is highly possible that the water trees as those that could emerge in the insulating cable made of XLPE cannot be reproduced exactly by the test using the test piece whose electrode holes have been created by the above-described method.

In view of such circumstances, a technique has been developed to reproduce water trees that are more similar to water trees that could emerge in an actual insulating cable used in liquid (Refer to Patent Document 2).

PRIOR ART DOCUMENTS

Patent Documents

[Patent Document 1] Japanese Patent Application Laid-Open Publication No. 2010-151576
[Patent Document 2] Japanese Patent Application Laid-Open Publication No. 2012-103158

SUMMARY OF THE INVENTION

Problems to be Solved by the Invention

The development of products for a rotary electric machine that employs a developed insulating cable with a resistance against the water tree phenomenon involves: reproducing the water tree phenomenon under the condition that it is used in target products; evaluating cable materials based on the results of the reproduction; an insulation design based on the results of the evaluation; and designing and producing a highly reliable rotary electric machine based on the results thereof. Accordingly, the time needed for the water-tree phenomenon reproduction test will greatly affect the product development time and the product cycle. Therefore, the time required to reproduce the water tree phenomenon should be as short as possible.

The object of the present invention therefore is to shorten the reproduction time required in the water-tree phenomenon reproduction test.

Means for Solving the Problem

According to the present invention, there is provided a water-tree resistance evaluation method for a water tree phenomenon of insulation material, comprising: a material selection step for selecting a candidate insulation material as a candidate; a test step for carrying out, after the material selection step, a water tree test on a test piece that is a flat plate made of the candidate insulation material selected by the material selection step and has electrode holes formed on a first surface; and a candidate insulation material evaluation step for evaluating, after the test step, characteristics of the candidate insulation material, including progress and speed of a water tree, based on a result of test at the test step, wherein the test step includes: a system and condition setting step for setting a test system so that the first surface of the test piece is immersed in an application-side aqueous solution of a voltage application side while a flat second surface of the test piece, which is an opposite side from the first surface, is immersed in a ground-side aqueous solution, a voltage application step for grounding, after the system and condition setting step, a ground-side electrode that is immersed in the ground-side aqueous solution, while applying an AC voltage to an application-side electrode that is immersed in the application-side aqueous solution, a measurement step for measuring, after the start of the voltage application step, progress of water tree inside the test piece at predetermined intervals, and a period determination step for determining, after the measurement step, whether a test period has exceeded a predetermined period, and for ending the test step if the test period has exceeded the predetermined period while repeating the voltage application step and subsequent steps if the test period has not exceeded the predetermined period.

According to the present invention, there is provided an insulation design method for designing in terms of insulation for a rotary electric machine in which voltage is applied at each component under operation, the method comprising: a material selection step for selecting a candidate insulation material as a candidate; a test step for carrying out, after the material selection step, a water tree test on a test piece that is a flat plate made of the candidate insulation material selected by the material selection step and has electrode holes formed on a first surface; a candidate insulation material evaluation step for evaluating, after the test step, characteristics of the candidate insulation material based on a result of test at the test step; and an insulation condition determination step for determining conditions for configuration of insulation of the rotary electric machine based on a result of evaluation at the candidate insulation material evaluation step and the voltage to be applied, wherein the test step includes a system and condition setting step for setting a test system so that the first surface of the test piece is immersed in an application-side aqueous solution of a voltage application side while a flat second surface of the test piece, which is an opposite side from the first surface, is immersed in a ground-side aqueous solution, a voltage application step for grounding, after the system and condition setting step, a ground-side electrode that is immersed in the ground-side aqueous solution, while applying an AC voltage to an application-side electrode that is immersed in the application-side aqueous solution, a measurement step for measuring, after the start of the voltage application step, progress of water tree inside the test piece at predetermined intervals, and a period determination step for determining, after the measurement step, whether a test period has exceeded a predetermined period, and of ending the test step if the test period has exceeded the predetermined period while repeating the voltage application step and subsequent steps if the test period has not exceeded the predetermined period.

Advantages of the Invention

According to the present invention, it is possible to shorten the reproduction time in the water-tree phenomenon reproduction test.

EMBODIMENTS FOR CARRYING OUT THE INVENTION

Hereinafter, with reference to the accompanying drawings, a water-tree resistance evaluation method and insulating design method of an embodiment of the present invention will be described. The same or similar portions are represented by the same reference symbols and will not be explained repeatedly.

Figure 1:
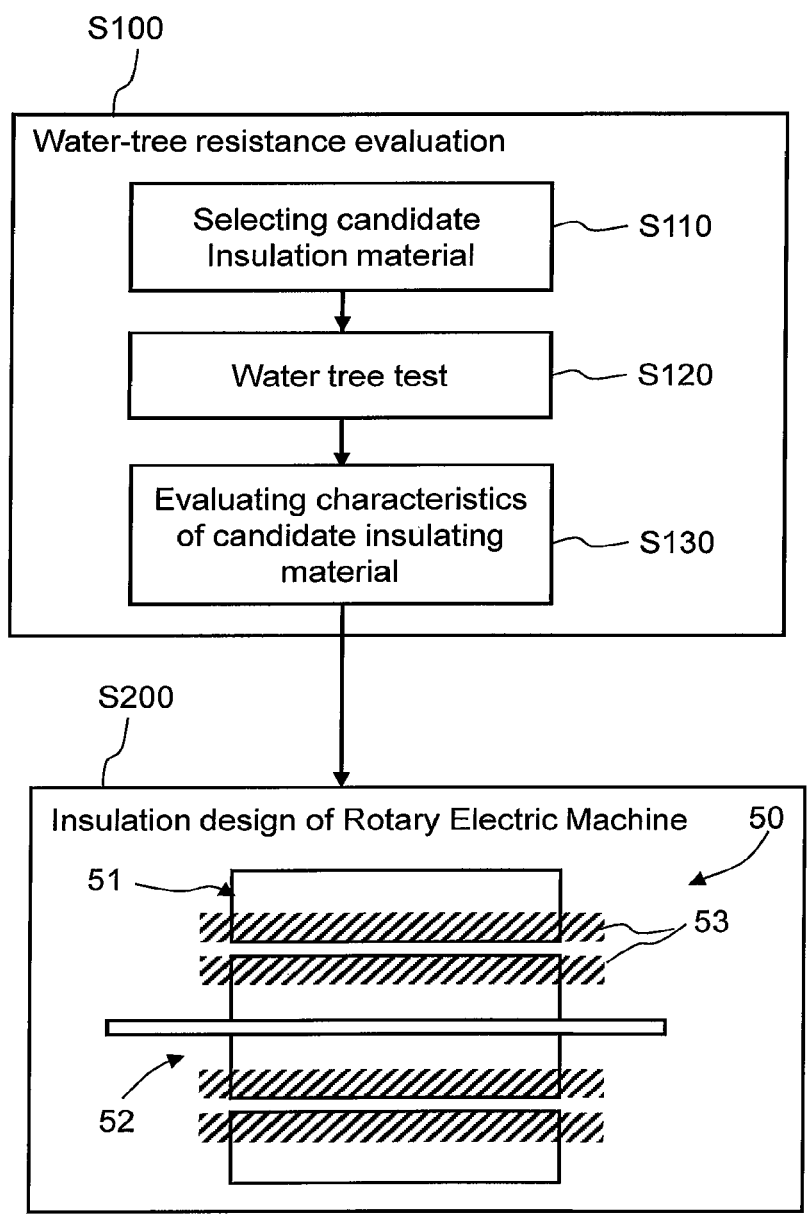
FIG. 1 is a flowchart showing the procedure of an insulation design method according to an embodiment.

FIG. 1 is a flowchart showing the procedure of an insulation design method according to the embodiment. The insulation design method generally includes a water-tree resistance evaluation step S100 of evaluating the resistance against water tree of an insulating material used in an insulating portion 53, such as coils of a stator 51 or a rotor 52 of a rotary electric machine 50; and an insulation design step S200 for the rotary electric machine.

The water-tree resistance evaluation step S100 includes a step (step S110) of selecting a candidate insulation material that is regarded as a candidate; a water tree test step (step S120) of carrying out a water tree test on the selected candidate insulation material; and a candidate insulation material evaluation step (step S130) of evaluating, in terms of insulation performance, characteristics of the candidate insulating material, which has been tested as a candidate, based on the results of the test.

Figure 2:
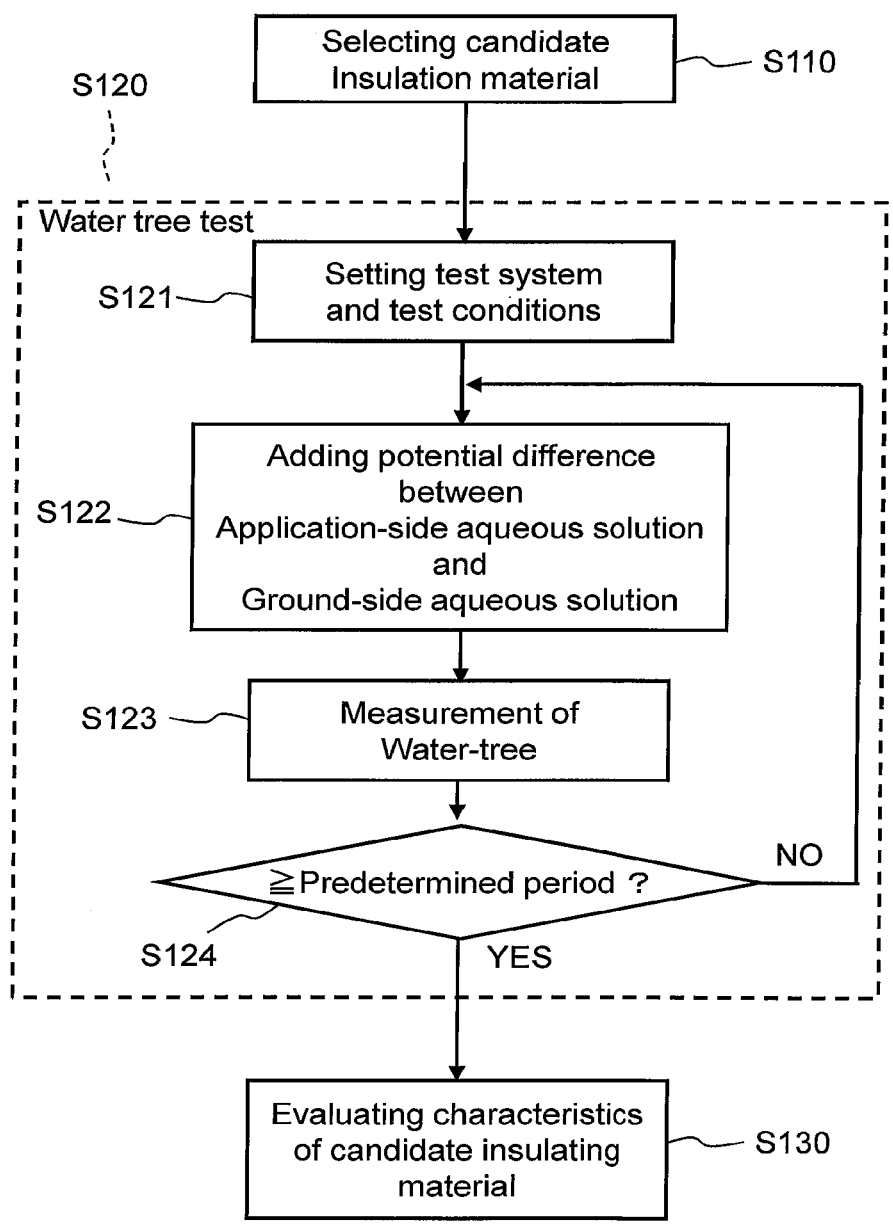
FIG. 2 is a flowchart showing the procedure of a water tree test by a water-tree resistance evaluation method according to an embodiment.

FIG. 2 is a flowchart showing the procedure of a water tree test by the water-tree resistance evaluation method according to the embodiment. At the water tree test step S120, first a test system and test conditions are set (Step S121). The test system and the test conditions will be detailed in an explanation of FIG. 3.

After step S121, voltage from an AC electrical source 40 (See FIG. 3) is applied to add a potential difference between an application-side aqueous solution 23 (See FIG. 3) and a ground-side aqueous solution 33 (See FIG. 3), and the voltage is applied to a test piece 10 (See FIG. 3) (Step S122).

After a certain period of time has passed since step S122, the progress of water tree is measured (Step S123). A determination is made as to whether or not a predetermined period of time, or a predetermined test period, has passed (Step S124). If the predetermined period of time has not passed (Step S124, NO), the step S122 and the subsequent process will be repeated. If the predetermined period of time has passed (Step S124, Yes), the test is ended.

Figure 3:
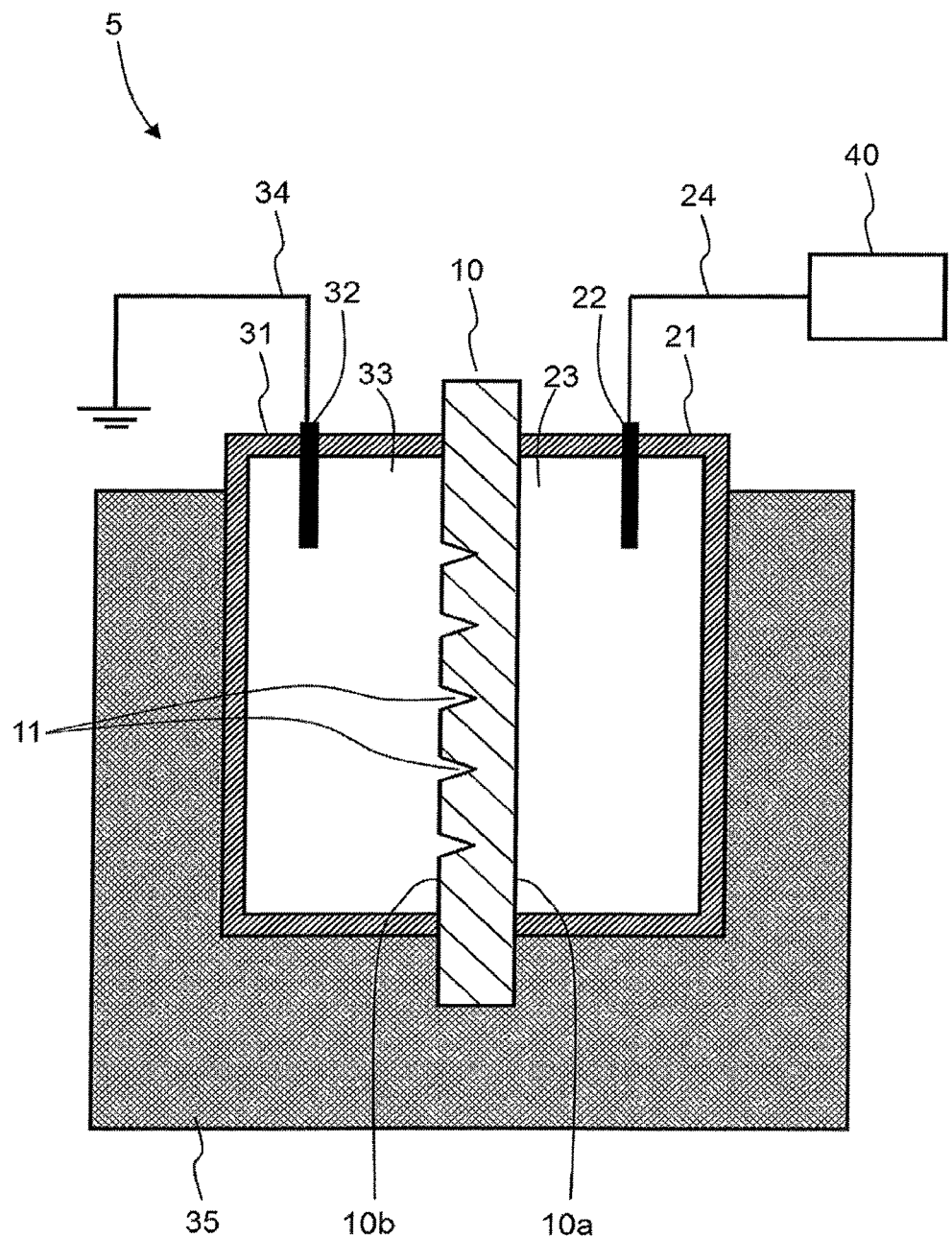
FIG. 3 is a sectional elevational view showing the configuration of a test device used for a reproduction test of a water tree phenomenon by a water-tree resistance evaluation method according to the embodiment.

FIG. 3 is a sectional elevational view showing the configuration of a test device used for a reproduction test of a water tree phenomenon by the water-tree resistance evaluation method according to the embodiment. A test apparatus 5 includes the test piece 10, an application-side water tank 21, an application-side electrode 22, a ground-side water tank 31, a ground-side electrode 32, and the AC electrical source 40. The application-side electrode 22 is connected to the AC electrical source 40 via conductor wires 24. The ground-side electrode 32 is connected to a ground point via a conductor wire 34. The application-side water tank 21 and the ground-side water tank 31 are metallic vessels. The tanks are not limited to the metallic vessels; the vessels may be made of polymer compound such as polyethylene.

The test piece 10 is made of an insulation material, such as cross-linked polyethylene (XLPE). The test piece 10 is a rectangular plate with some thickness. The test piece 10 includes, as wider planes, a first surface 10a and a second surface 10b. The first surface 10a and the second surface 10b are both flat and are formed in such a way as to be parallel to each other. On the second surface 10b, five electrode holes 11 are formed in such a way as to extend from the flat surface and to be perpendicular to that surface. The tips of the electrode holes 11 are made conical so that the holes gradually become smaller in cross-section toward the bottom. The electrode holes 11 are formed in such a way as to create a predetermined hole-depth-direction distance between the bottom portions and the first surface 10a. The number of electrode holes 11 is not limited to 5; the number may be set based on the statistical reliability of the test results and the like.

The electrode holes 11 may be made by pushing an object having sharp convex portions into the insulating material from the surface thereof. In such a case, the characteristics of the insulation material around the electrode holes 11 might be affected.

The electrode holes 11 may be made by a method by which insulating material is poured into a mold, for example. In this case, at a bottom surface of the mold used, convex portions that correspond to the shape of cavities of the electrode holes 11 are provided. Therefore, the shape of the electrode holes 11 is accurately formed. Moreover, the electrode holes 11 are formed without affecting the characteristics of the insulating material around the electrode holes 11.

In the test apparatus 5 of the present embodiment, the ground-side water tank 31 is attached in such a way as to cover part of the second surface 10b as well as all the electrode holes 11. A side of the ground-side water tank 31 that faces the second surface 10b is opened. In a region of the first surface 10a corresponding to a region of the second surface that is covered with the ground-side water tank 31, the application-side water tank 21 is attached. That is, in the test apparatus 5, the application-side water tank 21 and the ground-side water tank 31 are vessels whose one side is opened. The application-side water tank 21 and the ground-side water tank 31 are formed in such a way as to hold the test peace 10 between the application-side water tank 21 and the ground-side water tank 31.

In order to ensure the sealability of a contact portion of the open end of the application-side water tank 21 with the first surface 10a, as well as the sealability of a contact portion of the open end of the ground-side water tank 31 with the second surface 10b, an elastic material may be used for edges. Alternatively, the first surface 10a and the application-side water tank 21, or the second surface 10b and the ground-side water tank 31 may be pushed against each other via an O-ring or the like. A seal material or the like may be used to seal the gap between the open end of the application-side water tank 21 and the first surface 10a, and the gap between the ground-side water tank 31 and the second surface 10b.

Most of the test piece 10, the application-side water tank 21, and the ground-side water tank 31, except each of the upper portions, are covered with an insulation portion 35. This configuration prevents electrical contact with the outside of the test apparatus 5.

The application-side aqueous solution 23 is enclosed in the application-side water tank 21. The ground-side aqueous solution 33 is enclosed in the ground-side water tank 31. The application-side aqueous solution 23 and the ground-side aqueous solution 33 are neutral aqueous solutions. The application-side aqueous solution 23 and the ground-side aqueous solution 33 may be water.

The application-side electrode 22 is attached to the application-side water tank 21. The application-side electrode 22 extends and passes through a wall of the application-side water tank 21. One end of the application-side electrode 22 is located outside the application-side water tank 21, while the other end is immersed in the application-side aqueous solution 23 inside the application-side water tank 21. The end of the application-side electrode 22 that is located outside the application-side water tank 21 is connected to the AC electrical source 40.

The ground-side electrode 32 is attached to the ground-side water tank 31. The ground-side electrode 32 extends and passes through a wall of the ground-side water tank 31. One end of the ground-side electrode 32 is located outside the ground-side water tank 31, while the other end is immersed in the ground-side aqueous solution 33 inside the ground-side water tank 31. The end of the ground-side electrode 32 that is located outside the ground-side water tank 31 is connected to a portion that is grounded.

The voltage to be applied represents a value of voltage that the rotary electric machine 50 is supposed to be applied during operation. Particularly, insulation of coil conductor wires and the like are important. For example, as the voltages applied to the coil conductor wires, there are such voltages as line voltage, voltage to ground, and turn voltage. The values of these voltages and their frequencies may be theoretically obtained in advance from actual equipment, or may be experimentally measured.

Figure 4:
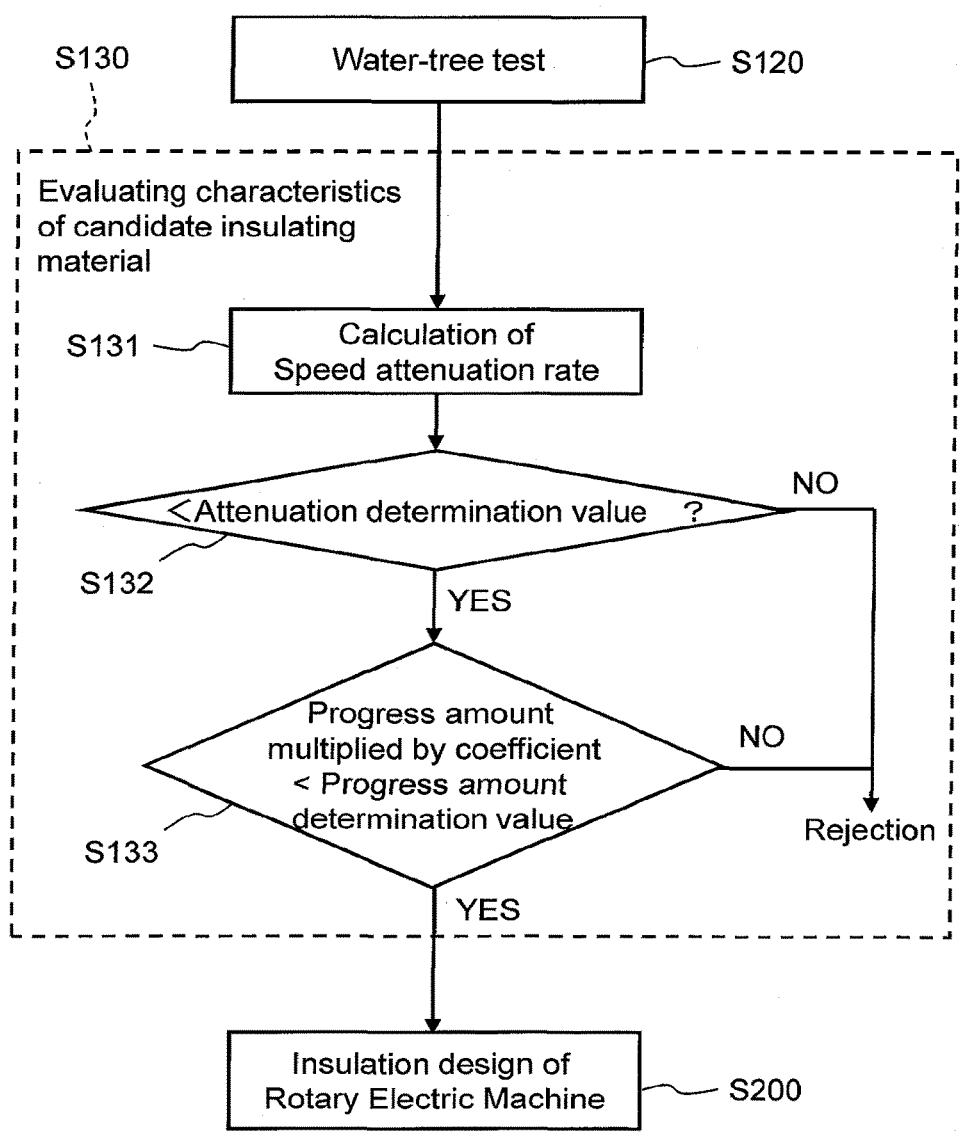
FIG. 4 is a flowchart showing the procedure of insulating material evaluation by a water-tree resistance evaluation method according to the embodiment.

FIG. 4 is a flowchart showing the procedure of insulating material evaluation by the water-tree resistance evaluation method according to the embodiment. In a candidate insulation material evaluation step S130, attenuation characteristics of the speed of progress of the water tree, or speed attenuation rate, is calculated (Step S131). The calculation is performed based on a change over time in the progress of water tree that is measured at step S123 (FIG. 2), at which the progress of water tree is measured in the water tree test step S120.

After step S131, a determination is made as to whether or not the speed attenuation rate is less than or equal to an attenuation determination value (Step S132). If the rate is neither less than nor equal to the attenuation determination value (Step S132, NO), the corresponding candidate insulation material is rejected.

If the speed attenuation rate at Step S132 is less than or equal to the attenuation determination value (Step S132, YES), the amount of the progress is multiplied by a predetermined coefficient, and then a determination is made as to whether or not the result is less than or equal to a progress amount determination value (Step S133). If the value, which is calculated by multiplying the amount of progress by the predetermined coefficient, is not less than or equal to the progress amount determination value (Step S133, NO), the corresponding candidate insulation material is rejected. If the value, which is calculated by multiplying the amount of progress by the predetermined coefficient, is less than or equal to the progress amount determination value (Step S133, YES), the process proceeds to the next step (step S200) for designing insulation of the rotary electric machine. At step S200, based on the results of evaluation by candidate insulation material evaluation step S130 as well as the voltage to be applied in the rotary electric machine 50, the insulation design is conducted. That is, conditions for the configuration of insulation of the rotary electric machine 50 are determined. After the insulation conditions are determined, the designing of specific structures and other factors pertaining to insulation is conducted.

The following explains what is going on at step S131, where the speed attenuation rate is calculated, as well as at step S133 where the determination is made after the amount of progress is multiplied by the predetermined coefficient.

Figure 5:
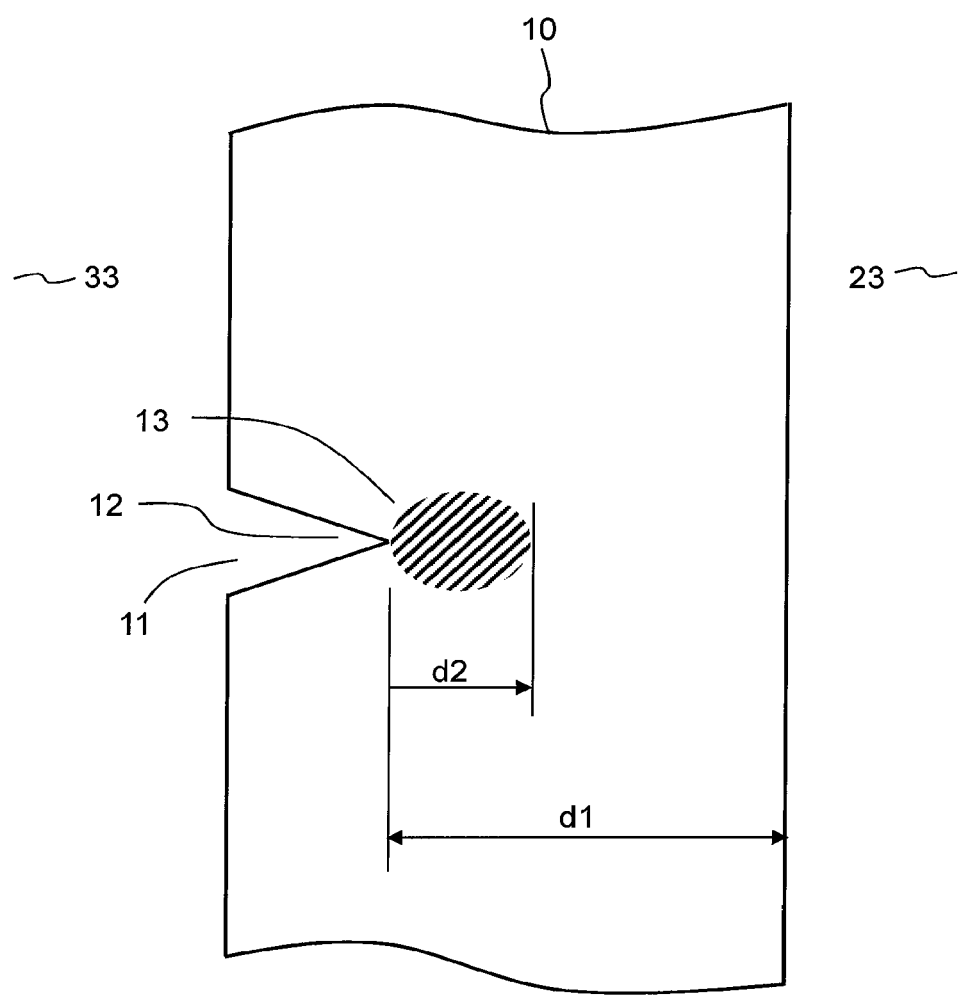
FIG. 5 is a sectional elevational view of part of a test body for explaining an evaluation method of reproduction-test results of a water tree phenomenon by a water-tree resistance evaluation method according to the embodiment.

FIG. 5 is a sectional elevational view of part of a test body for explaining an evaluation method of reproduction-test results of a water tree phenomenon by the water-tree resistance evaluation method according to the embodiment. A predetermined voltage is applied to a test piece 10 whose smallest portion has a thickness of d1. A certain number of days later, at the tip of a water electrode 12, a water tree portion 13 is observed. The progress of the water tree portion 13, or length d2 of the water tree portion 13, is measured by observing the cross-section of the test piece 10, which emerges as the test piece 10 is cut in a direction perpendicular to the test piece 10 at the position of the water electrode 12.

Accordingly, the test devices 5 shown in FIG. 3 are prepared for each of measurement operations. At the measurement timing, some of the test devices 5 are disassembled, and the test pieces 10 are cut for measurement.

Figure 6:
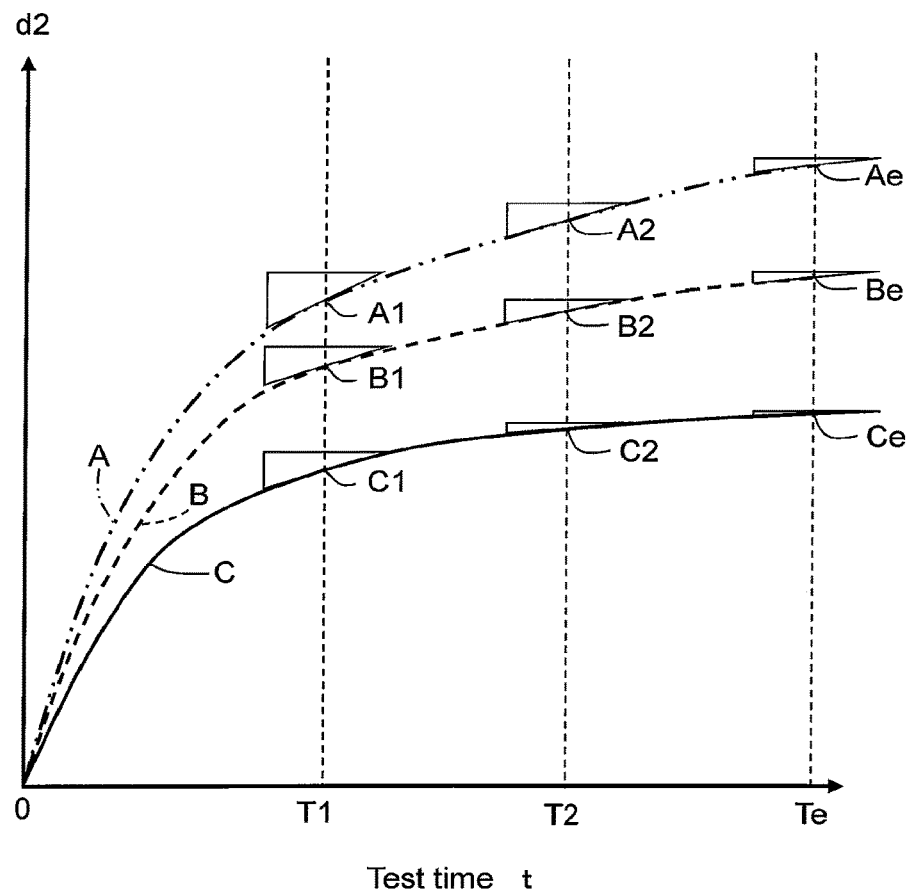
FIG. 6 is a first graph for explaining a saturation characteristics evaluation method based on reproduction-test results of a water tree phenomenon by a water-tree resistance evaluation method according to the embodiment.

FIG. 6 is a first graph for explaining a saturation characteristics evaluation method based on reproduction-test results of a water tree phenomenon by the water-tree resistance evaluation method according to the embodiment. The graph shows characteristic curves, which indicate the relation of progress d2 of water tree with respect to each of predetermined measurement times since the start of tests. Curve A represented by a two-dot chain line, curve B represented by a broken line, and curve C represented by a solid line are respectively characteristic curves created based on the measurement results of material A, material B, and material C. The horizontal axis represents the total time spent on the test since the start of the testing. Te represents the test time that lasts until the end of the testing. The vertical axis represents the progress d2 of water trees.

The slopes of the characteristic curves of materials A, B, and C at test time T1 are calculated, and the results are respectively referred to as A1, B1, and C1. The slopes of the characteristic curves A, B, and C at test time T2 are calculated, and the results are respectively referred to as A2, B2, and C2. The slopes of the characteristic curves A, B, and C at test end time Te are calculated, and the results are respectively referred to as Ae, Be, and Ce. The slopes of the characteristic curves A, B, and C at test time t=0, or at the start of the testing, are respectively represented by A0, B0, and C0. In a case where the characteristic curves rise after a dead time has passed since the start of the testing, the slopes of the greatest tilts of the rising portions are respectively referred to as A0, B0, and C0. In this case, the test time is at T1, T2, and Te. Instead, there may be more points in time at which data are sampled.

Figure 7:
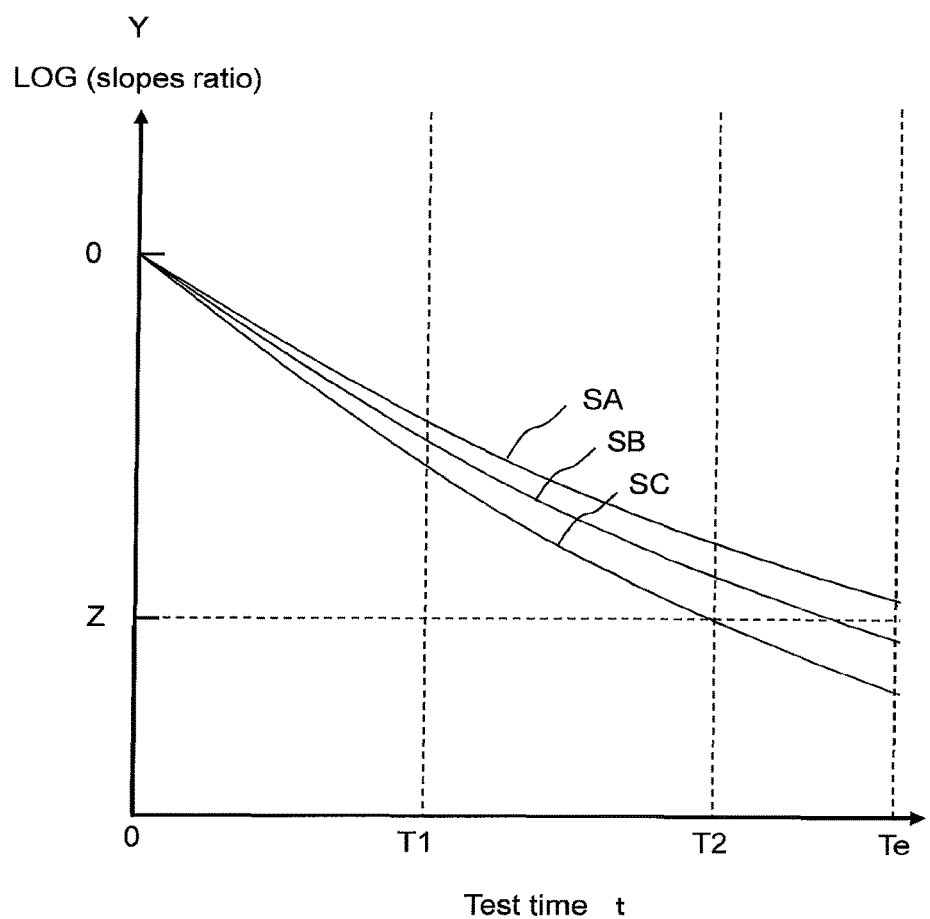
FIG. 7 is a second graph for explaining a saturation characteristics evaluation method based on reproduction-test results of a water tree phenomenon by a water-tree resistance evaluation method according to the embodiment.

FIG. 7 is a second graph for explaining a saturation characteristics evaluation method based on reproduction-test results of a water tree phenomenon by the water-tree resistance evaluation method according to the embodiment. The horizontal axis represents test time t. Vertical axis Y represents logarithmic values that are calculated by dividing slopes at each point in test time by the slope at time 0. For example, in the case of material A at test time T1, the following formula is established:

$$Y = \log_{10}(A1/A0) \quad (1)$$

Saturation determination curves SA, SB, and SC of materials A, B, and C are curves obtained based on Y-values at each point in time. The present invention is not limited to formula (1). Such a formula may not use logarithmic values if the formula is fit for determining the attenuation trend. Or such a formula may be of another kind of function. In this manner, the evaluation at step S131 is carried out.

Z shown in FIG. 7 is a determination value. If Y is less than Z at test time Te, or the end of the testing, then it is determined that saturation-characteristics requirements are satisfied. At step S132, a determination is made as to whether or not Y is less than Z at test time Te. For example, in the case of FIG. 7, the values of saturation determination curves SB and SC at test time Te are less than Z, and it is therefore determined that materials B and C have satisfied saturation-characteristics requirements.

Figure 8:
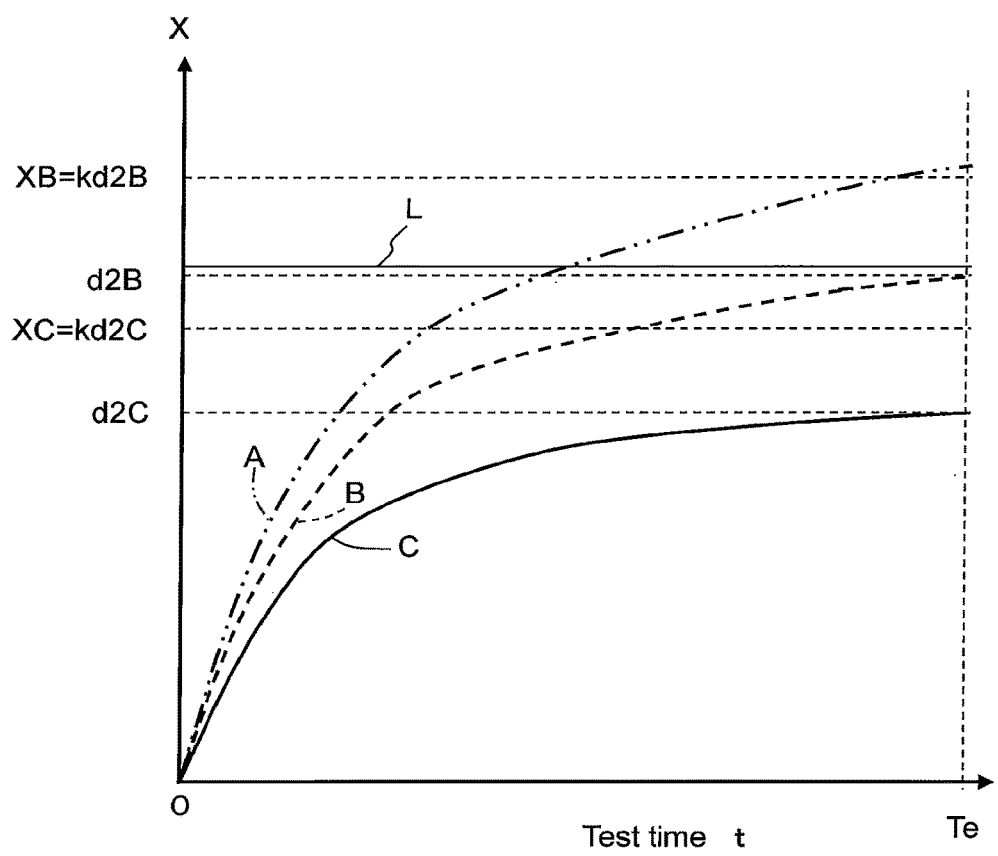
FIG. 8 is a graph for explaining a method of evaluating progress based on reproduction-test results of a water tree phenomenon by a water-tree resistance evaluation method according to the embodiment.

FIG. 8 is a graph for explaining a method of evaluating progress based on reproduction-test results of a water tree phenomenon by the water-tree resistance evaluation method according to the embodiment. The horizontal axis represents test time. The vertical axis represents progress d2 of a water tree and the like. In the diagram, value L is a progress amount determination value.

In the example of FIG. 8, the water-tree progress d2 at test time Te of materials B and C, which have been judged to have satisfied the saturation-characteristic requirements at step S132, are referred to as d2B and d2C, respectively. Moreover, k is a predetermined multiplier; k is set by taking into account variations in the characteristics of the insulation material, a difference between the test period and the trial period on actual equipment, and the like. The values obtained by multiplying d2B and d2C by k are respectively referred to as XB and XC. A determination is made as to whether or not XB and XC satisfy a limit of the magnitude of progress, based on whether or not XB and XC are less than progress amount determination value L. In this manner, the determination at step S133 is made.

For example, according to another determination method, x is defined in the following formula (2). A determination may be made as to whether or not the limit of the magnitude of progress is satisfied, based on whether or not the value of x is less than a predetermined percentage, which is for example 70 percent.

$$x = k \times (d2/d1) \times 100 \quad (2)$$

As described above, according to the present embodiment, voltage is applied via aqueous solution to the front and back sides of the test piece 10 to get water tree to progress without fail. As a result, it is possible to shorten the reproduction time required in the water-tree phenomenon reproduction test.

Moreover, during the test period, whether or not saturation condition has been reached is checked. As for the material of a test piece that has been judged to be saturated, the progress thereof is determined with a margin. Accordingly, a more reliable insulation design is possible. As a result of such an insulation design, the better quality of the rotary electric machine is ensured.

Other Embodiments

While embodiment of the present invention has been described, the embodiment has been presented by way of example only, and is not intended to limit the scope of the invention. Features of the embodiment may be used in combination.

Furthermore, the embodiment may be embodied in other various forms. Various omissions, replacements and changes may be made without departing from the spirit of the invention.

The embodiment and variants thereof are within the scope and spirit of the invention, and are similarly within the scope of the invention defined in the appended claims and the range of equivalency thereof.

EXPLANATION OF REFERENCE SYMBOLS

5: test apparatus, 10: test piece, 10a: first surface, 10b: second surface, 11: electrode holes, 12: water electrode, 13: water tree portion, 21: application-side water tank, 22: application-side electrode, 23: application-side aqueous solution, 24: conductor wire, 31: ground-side water tank, 32: ground-side electrode, 33: ground-side aqueous solution, 34: conductor wire, 35: insulation portion, 40: AC electrical source, 50: rotating electrical machine, 51: stator, 52: rotor, 53: insulating portion 53

The invention claimed is:

1. A water-tree resistance evaluation method for a water tree phenomenon of insulation material, comprising:
  selecting a candidate insulation material as a candidate;
  carrying out, after the selecting, a water tree test on a test piece that is a flat plate made of the candidate insulation material selected by the selecting and has electrode holes formed on a first surface; and
  evaluating, after the water tree test, characteristics of the candidate insulation material, including progress and speed of a water tree, based on a result of test at the water tree test, wherein
  the water tree test includes:
    setting a test system so that the first surface of the test piece is immersed in a ground-side aqueous solution of a voltage application side while a flat second surface of the test piece, which is an opposite side from the first surface, is immersed in an application-side aqueous solution,
    grounding, after the setting, a ground-side electrode that is immersed in the ground-side aqueous solution, while applying an AC voltage to an application-side electrode that is immersed in the application-side aqueous solution,
    measuring, after the start of the grounding and the applying, progress of water tree inside the test piece at predetermined intervals, and
    determining, after the measuring, whether a test period has exceeded a predetermined period, and for ending the water tree test if the test period has exceeded the predetermined period while repeating the grounding and the applying and the measuring if the test period has not exceeded the predetermined period;
  obtaining attenuation characteristics of a progress speed of water tree by dividing a slope of the progress speed at each point in test time by the slope at an initial time in the progress of the water tree obtained at the measuring;
  determining, after the attenuation characteristic evaluating, whether or not the attenuation characteristics satisfy attenuation determination conditions, and for rejecting the candidate insulation material if the attenuation determination conditions are not satisfied; and
  multiplying an amount of the progress by a predetermined coefficient if the attenuation characteristics satisfy the attenuation determination conditions at the determining, and of determining whether or not a value thereof is smaller than a progress amount determination value, and for rejecting the candidate insulation material if the value is not smaller than the progress amount determination value.

2. The water-tree resistance evaluation method according to claim 1, wherein
  the electrode holes are made after polymer material is heated to a predetermined temperature and poured into a mold member on which protruding portions corresponding to the electrode holes are formed and is hardened as the material is kept at a predetermined temperature and left for a predetermined time.

3. The water-tree resistance evaluation method according to claim 2, wherein
  the attenuation characteristic evaluating includes comparing either: a ratio of a temporal variation rate of the progress at final measurement time to a temporal variation rate of the progress immediately after the start of the measurement, or a logarithmic value of the ratio, with an attenuation determination value.

4. The water-tree resistance evaluation method according to claim 1, wherein
  the attenuation characteristic evaluating includes comparing either: a ratio of a temporal variation rate of the progress at final measurement time to a temporal variation rate of the progress immediately after the start of the measurement, or a logarithmic value of the ratio, with an attenuation determination value.

5. An insulation design method for designing in terms of insulation for a rotary electric machine in which voltage is applied at each component under operation, the method comprising:
  selecting a candidate insulation material as a candidate;
  carrying out, after the selecting, a water tree test on a test piece that is a flat plate made of the candidate insulation material selected by the selecting and has electrode holes formed on a first surface;
  evaluating, after the water tree test, characteristics of the candidate insulation material, including progress and speed of a water tree, based on a result of test at the water tree test; and
  determining conditions for configuration of insulation of the rotary electric machine based on a result of evaluating characteristics of the candidate insulation material and the voltage to be applied, wherein
  the water tree test includes:
    setting a test system so that the first surface of the test piece is immersed in a ground-side aqueous solution of a voltage application side while a flat second surface of the test piece, which is an opposite side from the first surface, is immersed in an application-side aqueous solution,
    grounding, after the setting, a ground-side electrode that is immersed in the ground-side aqueous solution, while applying an AC voltage to an application-side electrode that is immersed in the application-side aqueous solution,
    measuring, after the start of the grounding and the applying, progress of water tree inside the test piece at predetermined intervals, and
    determining, after the measuring, whether a test period has exceeded a predetermined period, and for ending the water tree test if the test period has exceeded the predetermined period while repeating the grounding and the applying and the measuring if the test period has not exceeded the predetermined period;

obtaining attenuation characteristics of a progress speed of water tree by dividing a slope of the progress speed at each point in test time by the slope at an initial time in the progress of the water tree obtained at the measuring;

determining, after the attenuation characteristic evaluating, whether or not the attenuation characteristics satisfy attenuation determination conditions, and for rejecting the candidate insulation material if the attenuation determination conditions are not satisfied; and multiplying an amount of the progress by a predetermined coefficient if the attenuation characteristics satisfy the attenuation determination conditions at the determining, and of determining whether or not a value thereof is smaller than a progress amount determination value, and for rejecting the candidate insulation material if the value is not smaller than the progress amount determination value.

* * * * *